United States Patent
Kirsch

(10) Patent No.: US 7,235,666 B2
(45) Date of Patent: Jun. 26, 2007

(54) PROCESS FOR THE PREPARATION OF SODIUM FOSPHENYTOIN

(75) Inventor: Volker Kirsch, Schaffhausen (CH)

(73) Assignee: Cilag Ltd., Schaffhausen (CH)

( * ) Notice: Subject to any disclaimer, the term of this patent is extended or adjusted under 35 U.S.C. 154(b) by 93 days.

(21) Appl. No.: 11/140,812

(22) Filed: May 31, 2005

(65) Prior Publication Data

US 2005/0272706 A1 Dec. 8, 2005

(30) Foreign Application Priority Data

Jun. 2, 2004 (CH) ....................... 929/04

(51) Int. Cl.
*C07F 9/6506* (2006.01)
*A61K 31/675* (2006.01)

(52) U.S. Cl. ......................... 548/112; 514/94
(58) Field of Classification Search ................ 548/112
See application file for complete search history.

(56) References Cited

U.S. PATENT DOCUMENTS 6,022,975 A * 2/2000 Davis et al. ................ 548/112
6,255,492 B1 * 7/2001 Davis et al. ................ 548/112

FOREIGN PATENT DOCUMENTS

CN 1379032 A * 11/2002
WO WO 97/41132 11/1997

OTHER PUBLICATIONS

March, J., Advanced Organic Chemistry, 4th Ed. John Wiley & Sons, 1992, pp. 352-357.*
CAS Abstract is provided for Wang et al. reference.*
Varia, S.A., et al., "Phenytoin Prodrugs III: Water-Soluble Prodrugs for Oral and/or Parenteral Use", Journal of Pharmaceutical Sciences, vol. 73, No. 8, 1068-1073 (1984).

* cited by examiner

*Primary Examiner*—Kamal A. Saeed
*Assistant Examiner*—Jason M. Nolan
(74) *Attorney, Agent, or Firm*—Hoffmann & Baron, LLP

(57) ABSTRACT

Phosphoric acid diester 2,5-dioxo-4,4-diphenylimidazolidin-1-ylmethyl esters, both of whose ester groups can be selectively cleaved, are obtained by converting 3-(hydroxymethyl)-5,5-diphenylimidazolidine-2,4-dione to an alkylsulfonate or arylsulfonate and reacting this with a phosphoric acid diester whose ester groups can be selectively cleaved from the reaction product.

The two ester groups can be selectively cleaved from the phosphoric acid diesters obtained and the resulting product can be converted to 5,5-diphenyl-3-[(phosphonooxy)methyl]imidazolidine-2,4-dione disodium salt. The latter is an anticonvulsive, antiepileptic and antiarrhythmic known under the abbreviated name of sodium fosphenytoin.

21 Claims, No Drawings

PROCESS FOR THE PREPARATION OF SODIUM FOSPHENYTOIN

Sodium fosphenytoin is the abbreviated name for 5,5-diphenyl-3-[(phosphono-oxy)methyl]imidazolidine-2,4-dione disodium salt, which is used as an anticonvulsive, antiepileptic and antiarrhythmic. Preparations containing sodium fosphenytoin are marketed under the name of Cerebyx.

According to the original literature synthesis (J. Pharm. Sci. 1984, 73(8), 1068-1073), sodium fosphenytoin is prepared by converting hydroxymethyiphenytoin, i.e. 3-(hydroxymethyl)-5,5-diphenylimidazolidine-2,4-dione, to 3-chloromethylphenytoin, reacting this with silver dibenzylphosphonate, cleaving the two benzyl groups in the resulting diester by catalytic hydrogenation and, finally, forming the desired disodium salt by means of sodium hydroxide solution. According to EP 0 900 227 B1, diesters of said type can be prepared, without needing to use a silver salt, by reacting 3-chloromethylphenytoin or 3-bromomethyiphenytoin with an alkali metal phosphonate such as potassium or sodium dibenzylphosphonate.

It has now been found that sodium fosphenytoin can advantageously be prepared by converting 3-(hydroxymethyl)-5,5-diphenylimidazolidine-2,4-dione to an alkylsulfonate or arylsulfonate, reacting this with a phosphoric acid diester whose ester groups can be selectively cleaved from the reaction product, cleaving the ester groups from the resulting phosphoric acid diester 2,5-dioxo-4,4-diphenylimidazolidin-1-ylmethyl ester and converting the resulting 5,5-diphenyl-3-[(phosphonooxy)methyl]imidazolidine-2,4-dione to its disodium salt.

Suitable alkylsulfonates or arylsulfonates of 3-(hydroxymethyl)-5,5-diphenylimidazolidine-2,4-dione are the mesylate, tosylate, besylate, nosylate, trifluoromethylsulfonate and the like; the mesylate is preferred.

The conversion of 3-(hydroxymethyl)-5,5-diphenylimidazolidine-2,4-dione to an alkylsulfonate or arylsulfonate is advantageously effected by means of a corresponding alkylsulfonyl or arylsulfonyl chloride such as mesyl chloride, in the presence of a suitable base, advantageously a trisubstituted aliphatic amine such as triethylamine, trimethylamine, tributylamine, ethyldiisopropylamine, N-methylmorpholine or the like, and preferably triethylamine, in an inert polar organic solvent such as tetrahydrofuran, N,N-dimethylformamide, N,N-dimethylacetamide, dimethyl sulfoxide, 1,3-dimethylimidazolidin-2-one, 1-methylpyrrolidin-2-one, dichloromethane or the like, and preferably tetrahydrofuran. It is advantageous to use about 1.0 to about 5.0 equivalents, preferably about 1.1 to about 1.4 equivalents, of sulfonylating agent and about 2.0 to about 20.0 equivalents, preferably about 2.1 to about 5.0 equivalents, of base, based on the 3-(hydroxymethyl)-5,5-diphenylimidazolidine-2,4-dione.

Particularly suitable ester groups which can be selectively cleaved from the reaction product are those which can be cleaved under mild acidic conditions (e.g. tert-butyl or 2,2,2-trichloroethyl), oxidatively (e.g. silylated alkyl groups), under mild basic conditions (e.g. ethyl) or photochemically (e.g. nitrobenzyl), but especially groups which can be cleaved by hydrogenolysis, such as the benzyl group and substituted benzyl groups like 4-methoxybenzyl, 4-bromobenzyl, 2-methoxybenzyl, 2,4-dimethoxybenzyl, etc. The ester groups are advantageously identical. Phosphoric acid diesters whose ester groups can be selectively cleaved from the reaction product are especially ditert-butyl phosphate, dibenzyl phosphate, bis-4-methoxybenzyl phosphate, bis-4-bromobenzyl phosphate, bis-4-nitrobenzyl phosphate, bis(2,4-dimethoxybenzyl) phosphate, bis-2,2,2-trichloroethyl phosphate, bis(2-trimethylsilylethyl) phosphate or diallyl phosphate, as well as dimethyl phosphate or diethyl phosphate. Dibenzyl phosphate is preferred.

It is advantageous to use about 0.5 to 10.0 equivalents, preferably about 1.0 to 1.5 equivalents, of phosphoric acid diester, based on the 3-(hydroxymethyl)-5,5-diphenylimidazolidine-2,4-dione.

The reaction temperature for both the sulfonylation and the reaction of the sulfonylation product with the phosphoric acid diester is about −30 to about +80° C., preferably about −10 to about +30° C.

The phosphoric acid diesters used in the process according to the invention are known or are easily accessible by processes familiar to all those skilled in the art.

The reaction of the alkylsulfonate or arylsulfonate of 3-(hydroxymethyl)-5,5-diphenylimidazolidine-2,4-dione with the phosphoric acid diester advantageously takes place in an inert polar organic solvent such as tetrahydrofuran, N,N-dimethylformamide, N,N-dimethylacetamide, dimethyl sufoxide, 1,3-dimethylimidazolidin-2-one, 1-methylpyrrolidin-2-one, dichloromethane or the like, and preferably tetrahydrofuran. Said alkylsulfonate or arylsulfonate does not need to be isolated, but can be reacted in situ with the phosphoric acid diester, particularly as the same solvent, i.e. preferably tetrahydrofuran, can be used for its preparation and for its further processing.

The resulting phosphoric acid diester 2,5-dioxo-4,4-diphenylimidazolidin-1-ylmethyl ester is advantageously worked up or isolated from an organic solvent such as toluene, ethyl acetate, acetone or the like.

The further processing of the phosphoric acid diester 2,5-dioxo-4,4-diphenylimidazolidin-1-ylmethyl ester is then carried out in conventional manner, the ester groups being cleaved and the resulting 5,5-diphenyl-3-[(phosphonooxy)-methyl]imidazolidine-2,4-dione being converted to its disodium salt. Thus, phosphoric acid 2,5-dioxo-4,4-diphenylimidazolidin-1-ylmethyl dibenzyl ester can be catalytically hydrogenated, for example on Pd/C in ethyl acetate, and the resulting 5,5-diphenyl-3-[(phosphonooxy)methyl]imidazolidine-2,4-dione can be converted to its disodium salt by means of sodium hydroxide solution.

A preferred embodiment of the process according to the invention can be represented by the reaction scheme below:

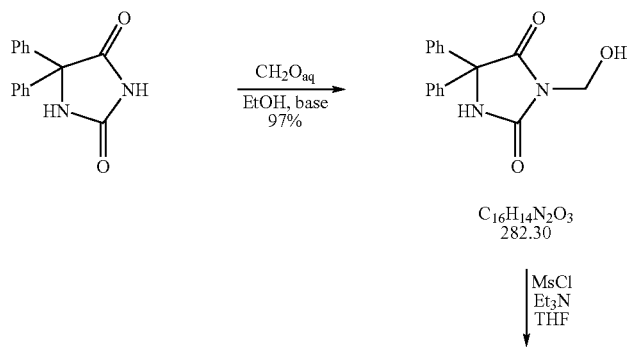

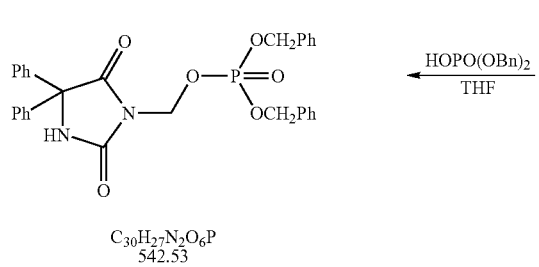

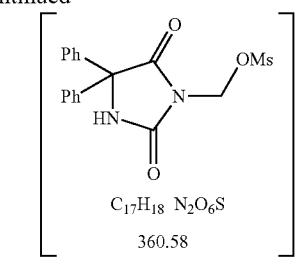

-continued

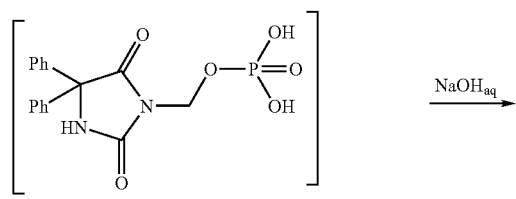

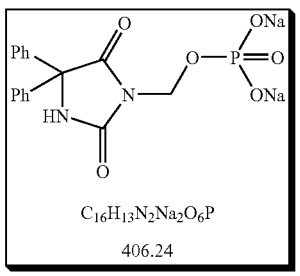

In contrast to the processes known hitherto (cf. EP 0 900 227, for instance), in the process according to the invention the chloride (or bromide) is replaced by the corresponding mesylate (or another, optionally substituted alkylsulfonate or arylsulfonate such as the tosylate, besylate, nosylate, trifluoromethylsulfonate or the like). Unlike the halide, the sulfonate does not have to be isolated, but can be reacted further in situ. Compared with known syntheses, the isolation of an intermediate is therefore superfluous. Furthermore, under the reaction conditions applied, a sulfonate is substantially more reactive than a halide, so the reaction is preferable. The chloride known from the literature is formed in small amounts as a by-product during the reaction with the sulfonyl chloride such as mesyl chloride, and it can still be detected after the sulfonate, e.g. mesylate, has completely reacted. Evidence of the unsatisfactory reaction behaviour of chloride is the addition of catalytic amounts of potassium iodide (0.3% by weight, based on the alkali metal phosphonate), according to the literature, in order to accelerate the reaction. The addition of potassium iodide increases the cost of the reaction and introduces additional foreign salt into the mixture.

Also, the process according to the invention uses not an alkali metal phosphonate but a correspondingly doubly protected (i.e. esterified), free phosphoric acid (e.g. dibenzyl phosphate). This enters into a partial intermediate reaction with the base, such as triethylamine, already used for deprotonation in the sulfonylation (e.g. mesylate formation) to give the corresponding ammonium salt (e.g. triethylammonium salt). The use of a free acid compared with its alkali metal salt has the advantage that (apart from better commercial availability) no additional foreign ions are introduced into the mixture. Moreover, the solubility of the doubly esterified, free phosphoric acid and ammonium salts (e.g. its triethylammonium salt) in organic solvents is better than that of corresponding alkali metal salts.

It is preferable to use the dibenzyl ester of phosphoric acid because the protecting groups are easy to cleave, but it is also possible to use any other ester having protecting groups which can be selectively cleaved.

The further processing to sodium fosphenytoin then proceeds according to the original literature synthesis (J. Pharm. Sci. 1984, 73(8), 1068-1073) or by another known process.

In contrast to known processes, which, starting from hydroxymethylphenytoin, require a further four steps to obtain the product (activation of hydroxymethylphenytoin, coupling, cleavage of benzyl protecting groups, salting), the process according to the invention requires only three working steps because isolation of the sulfonate (e.g. the mesylate) is superfluous.

In contrast to the process according to U.S. Pat. No. 6,022,975, which produces sodium fosphenytoin from hydroxymethylphenytoin in a yield of about 57%, the process according to the invention is capable of producing sodium fosphenytoin, likewise from hydroxymethylphenytoin, in a yield of about 65%.

In the process according to U.S. Pat. No. 6,022,975, the chlorination is carried out in a mixture of ethyl acetate and N,N-dimethylformamide (DMF), the isolation of the chloride is carried out in heptane, the coupling is carried out in acetonitrile and the isolation of the coupling product is carried out in toluene. However, in the preferred embodiment of the process according to the invention, represented in the scheme above, only one solvent, namely tetrahydrofuran (THF), is needed for mesylation and coupling, and the product can be isolated from e.g. toluene, ethyl acetate or acetone, thereby reducing the total number of solvents used as well as their total amount. Also, in contrast to the process according to U.S. Pat. No. 6,022,975, very toxic solvents (acetonitrile, DMF) and/or expensive solvents (heptane) do not have to be used according to the invention.

It is seen from the three points listed above, namely fewer working steps, higher yield and fewer solvents of lower toxicity and cost, that the process according to the invention is more economic than the process according to U.S. Pat. No. 6,022,975 (and of course much more economic than any earlier processes using silver salts of phosphates).

The process according to the invention offers a novel way of synthesizing fosphenytoin disodium salt. It is surprising here that the alkylsulfonates or arylsulfonates used are substantially more reactive than the halides mentioned in the literature, reacting smoothly without the addition of a catalyst (potassium iodide). This makes the process according to the invention more economic and simpler.

It is likewise surprising that—in contrast to the halides according to the state of the art—the alkylsulfonate or arylsulfonate does not have to be isolated, but can be directly coupled with dibenzyl phosphate, it being unnecessary to change either the base (e.g. triethylamine) used for the sulfonation (e.g. mesylation) or the solvent (e.g. tetrahydrofuran), which serve the same functions in the subsequent step. It has thus been possible to combine both stages into a true one-pot reaction, again making the process more economic and simpler. Finally, a salt can be replaced by the doubly esterified, free phosphoric acid. These unexpected advantages have afforded a marked simplification and improvement of the processes described in the literature.

Possible variations for individual parameters of the reaction sequence have been given above. Possible ways of varying the parameters have been indicated, but these do not imply any limitation. The Examples which follow are intended to illustrate the invention in greater detail, but without in any way restricting its scope.

EXAMPLE 1

Phosphoric Acid 2,5-dioxo-4,4-diphenylimidazolidin-1-ylmethyl Dibenzyl Ester 5.0 g (17.7 mmol) of 3-(hydroxymethyl)-5,5-diphenylimidazolidine-2,4-dione (hydroxymethylphenytoin) and 7.5 g (74.1 mmol) of triethylamine were dissolved in 30 g of tetrahydrofuran (THF). A solution of 2.4 g (21.0 mmol) of methanesulfonyl chloride in 33.3 g of THF was added at −10 to −5° C. A white suspension formed. The suspension was filtered and the clear filtrate was added to a suspension of 5.8 g (20.8 mmol) of dibenzyl phosphate in 5.0 g of THF at room temperature. After stirring overnight, the mixture was concentrated on a rotary evaporator, 50 g of ethyl acetate and 25 g of water were then added to the residue and the phases were separated. The organic phase was washed once with 20 g of water and then extensively concentrated on a rotary evaporator. 2.5 g of acetone and seed material were added to the residue obtained and the mixture was stirred overnight at 0 to 10° C. The resulting colourless precipitate was filtered off and dried under vacuum. Yield: 6.9 g (72%).

EXAMPLE 2

5,5-Diphenyl-3-[(phosphonooxy)methyl]imidazolidine-2,4-dione Disodium Salt (Sodium Fosphenytoin)

The product obtained according to Example 1 (6.9 g, 12.7 mmol) is catalytically hydrogenated on 0.5 g of Pd/C in 100 ml of ethyl acetate. The catalyst is filtered off and the filtrate is concentrated. The 5,5-diphenyl-3-[(phosphonooxy)methyl]-imidazolidine-2,4-dione obtained is taken up in 50 ml of methanol and converted to its disodium salt by the addition of 4.0 g of 30% sodium hydroxide solution. The suspension formed is cooled and filtered and the material on the filter is washed with a little methanol/water. The product is recrystallized from water/acetone if necessary. Yield: 4.15 g (1.5 mmol, 90

What is claimed is:

1. A process for the preparation of phosphoric acid diester 2,5-dioxo-4,4-diphenylimidazolidin-1-ylmethyl esters, wherein 3-(hydroxymethyl)-5,5-diphenylimidazolidine-2,4-dione is converted to an alkylsulfonate or arylsulfonate and this is reacted with a phosphoric acid diester whose ester groups can be selectively cleaved from the reaction product, wherein the alkylsulfonation or arylsulfonation of said 3-hydroxymethyl-5,5-diphenyl-imidazolidine-2,4-dione and the reaction of said alkylsulfonylation or arylsulfonylation product with said phosphoric acid diester is carried out in the presence of trisubstituted aliphatic amine base, at a temperature of −10° C. to +30° C. and in the presence of polar aprotic solvent, said solvent being selected from the group consisting of tetrahydrofuran, N,N-dimethylformamide, N,N-dimethylacetamide, dimethyl sulfoxide, 1,3-dimethylimidazolidin-2-one, 1-methylpyrrolidin-2-one and dichloromethane.

2. The process of claim 1, wherein the 3-(hydroxymethyl)-5,5-diphenylimidazolidine-2,4-dione is converted to its mesylate, tosylate, besylate, nosylate or trifluoromethylsulfonate.

3. The process of claim 2, wherein the 3-(hydroxymethyl)-5,5-diphenylimidazolidine-2,4-dione is converted to the mesylate.

4. The process of claim 1, wherein an alkyl-sulfonyl or arylsulfonyl chloride is used as the alkylsulfonylating or arylsulfonylating agent.

5. The process of claim 1, wherein 1.0 to 5.0 equivalents of sulfonylating agent are used, based on the 3-(hydroxymethyl)-5,5-diphenylimidazolidine-2,4-dione.

6. The process of claim 5, wherein 1.1 to 1.4 equivalents of sulfonylating agent are used, based on the 3-(hydroxymethyl)-5,5-diphenyl-imidazolidine-2,4-dione.

7. The process of claim 1, wherein triethylamine, trimethylamine, tributylamine, ethyldiisopropylamine or N-methylmorpholine is used as said trisubstituted aliphatic amine.

8. The process of claim 7, wherein triethylamine is used as said trisubstituted aliphatic amine.

9. The process of claim 1, wherein 2.0 to 20.0 equivalents of base are used, based on the 3-(hydroxymethyl)-5,5-diphenyl-imidazolidine-2,4-dione.

10. The process of claim 9, wherein 2.1 to 5.0 equivalents of base are used, based on the 3-(hydroxymethyl)-5,5-diphenylimidazolidine-2,4-dione.

11. The process of claim 1, wherein the alkylsulfonate or arylsulfonate of 3-(hydroxymethyl)-5,5-diphenylimidazolidine-2,4-dione is reacted with a phosphoric acid diester whose ester groups can be cleaved under mild acidic conditions, oxidatively, photochemically, under mild basic conditions or by hydrogenolysis.

12. The process of claim 11, wherein the phosphoric acid diester contains two identical ester groups.

13. The process of claim 11, wherein the ester groups can be cleaved by hydrogenolysis.

14. The process of claim 12, wherein dibenzyl phosphate, bis(4-methoxybenzyl) phosphate, bis(4-bromobenzyl) phosphate, bis(2-methoxybenzyl) phosphate or bis(2,4-dimethoxy-benzyl) phosphate is used.

15. The process of claim 14, wherein dibenzyl phosphate is used.

16. The process of claim 1, wherein 0.5 to 10.0 equivalents of phosphoric acid diester are used, based on the 3-(hydroxymethyl)-5,5-diphenylimidazolidine-2,4-dione.

17. The process of claim 16, wherein 1.0 to 1.5 equivalents of phosphoric acid diester are used, based on the 3-(hydroxymethyl)-5,5-diphenyl-imidazolidine-2,4-dione.

18. The process of claim 1, wherein the same solvent is used for the alkylsulfonylation or arylsulfonylation of the 3-(hydroxymethyl)-5,5-diphenylimidazolidine-2,4-dione and for the reaction of the alkylsulfonylation or arylsulfonylation product with the phosphoric acid diester.

19. The process of claim 1, wherein the alkylsulfonylation or arylsulfonylation product is not isolated, but reacted in situ with the phosphoric acid diester.

20. The process of claim 1, wherein tetrahydrofliran is used as the solvent.

21. The process of claim 1, wherein the two ester groups are selectively cleaved from the phosphoric acid diester 2,5-dioxo-4,4-diphenylimidazolidin-1-ylmethyl ester obtained and the resulting compound is converted to 5,5-diphenyl-3-[(phosphonooxy)methyl]imidazolidine-2,4-disodium salt.

* * * * *

UNITED STATES PATENT AND TRADEMARK OFFICE
CERTIFICATE OF CORRECTION

PATENT NO. : 7,235,666 B2  
APPLICATION NO. : 11/140812  
DATED : June 26, 2007  
INVENTOR(S) : V. Kirsch Page 1 of 1

It is certified that error appears in the above-identified patent and that said Letters Patent is hereby corrected as shown below:

At column 8, claim 20, line 1, the printed patent should read --...wherein tetrahydrofuran is...--.

Signed and Sealed this

Fourteenth Day of August, 2007

JON W. DUDAS  
*Director of the United States Patent and Trademark Office*